United States Patent
Hoe

(12) 
(10) Patent No.: US 11,583,207 B2
(45) Date of Patent: Feb. 21, 2023

(54) APPARATUS FOR MEASUREMENT OF A LIMB CIRCUMFERENCE, A DEVICE FOR MEASUREMENT OF A LIMB COMPLIANCE COMPRISING THE SAME AND A DEVICE USED IN THE TREATMENT OF LYMPHEDEMA COMPRISING THE SAME

(71) Applicant: Yer-Yian Hoe, Kaohsiung (TW)

(72) Inventor: Yer-Yian Hoe, Kaohsiung (TW)

(73) Assignee: Yer-Yian Hoe, Kaohsiung (TW)

( * ) Notice: Subject to any disclaimer, the term of this patent is extended or adjusted under 35 U.S.C. 154(b) by 782 days.

(21) Appl. No.: 16/516,408

(22) Filed: Jul. 19, 2019

(65) Prior Publication Data
US 2020/0029860 A1   Jan. 30, 2020

(30) Foreign Application Priority Data

Jul. 25, 2018   (TW) .................................. 107125791
Jul. 16, 2019   (TW) .................................. 108125106

(51) Int. Cl.
*A61B 5/107* (2006.01)
*G01B 5/02* (2006.01)
*A61B 5/00* (2006.01)

(52) U.S. Cl.
CPC .......... *A61B 5/1073* (2013.01); *A61B 5/0002* (2013.01); *A61B 5/1072* (2013.01); *A61B 5/1075* (2013.01); *A61B 5/1079* (2013.01); *G01B 5/025* (2013.01)

(58) Field of Classification Search
CPC ... A61B 5/1073; A61B 5/1072; A61B 5/1075; A61B 5/1079; G01B 5/025
See application file for complete search history.

(56) References Cited

FOREIGN PATENT DOCUMENTS

KR       101791495 B1  *  10/2017  ........... A61B 5/0077

OTHER PUBLICATIONS

Machine translation of KR 101791495 B1 (Year: 2017).*

* cited by examiner

*Primary Examiner* — Devin B Henson
(74) *Attorney, Agent, or Firm* — Amin, Turocy & Watson LLP

(57) ABSTRACT

The present invention provides an apparatus for measurement of a limb circumference, comprising a pull string module, a first measurement module and a second measurement module. The pull string module comprises a surrounding component, wherein the surrounding component comprises an encircling part disposed around a limb of an individual; the first measurement module is disposed at the pull string module and moves alone the longitudinal axis of the limb and meanwhile measures the length of the limb; and the second measurement module measures the length of the encircling part simultaneously when the first measurement module move alone the limb, so as to determine the correlation between the limb length and the limb circumference. The present invention further provides a device including two or more apparatuses of the present invention to measure the limb compliance and to be used in the treatment of lymphedema.

6 Claims, 9 Drawing Sheets

APPARATUS FOR MEASUREMENT OF A LIMB CIRCUMFERENCE, A DEVICE FOR MEASUREMENT OF A LIMB COMPLIANCE COMPRISING THE SAME AND A DEVICE USED IN THE TREATMENT OF LYMPHEDEMA COMPRISING THE SAME

RELATED APPLICATIONS

The present application claims the priority of Taiwan Applications No. 107125791, filed Jul. 25, 2018, and No. 108125106, filed Jul. 16, 2019, the disclosure of which are hereby incorporated by reference herein in its entirety.

BACKGROUND OF THE INVENTION

1. Field of the Invention

The present disclosure generally relates to an apparatus for measurement of a limb circumference, more particularly, to an detection apparatus for continuously and thoroughly measuring the circumference of a limb and for measurement of a limb compliance and a device for treatment of lymphedema of a limb.

2. Description of the Related Art

Fibrosis is caused by the lymph node dissection and/or radiation therapy during the treatment of cancer, such as breast cancer, gynecologic cancer or pelvic tumor. It may lead to a blockage of the lymphatic system resulting in a condition of localized fluid retention and tissue swelling, which is called lymphedema which is commonly seen in limbs.

Lymphedema is caused by the unbalance of the lymph flowing through the lymphatic system. In many patients with cancer, this condition does not develop until months or even years after therapy has concluded. Lymphedema would have severely effect on the patients' appearance, confidence, and their daily self-management.

Given the good therapeutic effect of lymphedema at early stage, an easy-to-use device for measuring the limb circumference is urgently needed by the patients after surgery, chemotherapy and/or radiation therapy to determine if lymphedema occurs or not. Besides, the medical personnel could modify the therapy according to the data of the patients' limb circumference, which would be more suitable for the patients.

Moreover, according to clinical experience, it is necessary to measure the limb compliance which reflects the internal pressure in extremities and may be indices of the change of the stages of lymphedema and of the therapeutic effect. It is found that lymphedema could be relieved by manual lymph drainage (MLD). However, MLD has to be performed by trained professionals. Not only does it cost immense manpower, but the therapy can be conducted in registered medical institutions. It is in urgent need of developing a device to achieve the above desired therapeutic effect. That would save labor cost with no restriction to time and place.

Consequently, it is an issue to be overcome in the industry to develop a detection device for measurement of limb circumference and compliance and can be used in the treatment of lymphedema.

SUMMARY OF THE INVENTION

The present invention provides an apparatus for measurement of a limb circumference, comprising a pull string module, a first measurement module, and a second measurement module. The pull string module comprises a surrounding component, wherein the surrounding component comprises an encircling part disposed around a limb of an individual; the first measurement module is disposed at the pull string module, and wherein the first measurement module is used to move alone the longitudinal axis of the limb and meanwhile measure the length of the limb; and the second measurement module is disposed at the pull string module, and the second measurement module is used to measure the length of the encircling part simultaneously when the first measurement module move alone the limb, so as to determine the limb circumference.

In an embodiment of the present inventive concept, the pull string module further comprises a constant-force spring set; and a connecting wire having two ends, wherein one end of the connecting wire is connected to the constant-force spring set; and wherein the surrounding component is a bead chain, and the bead chain is connected to the other end of the connecting wire.

In an embodiment of the present inventive concept, the first measurement module comprises a roller connected to the bead chain and a first angle detector connected to the roller. The roller is used to roll alone the longitudinal axis of the limb; and the first angle detector is used to measure the rotation angle of the roller.

In an embodiment of the present inventive concept, the second measurement module comprises a ratchet disposed on the bead chain and a second angle detector connected to the ratchet. The ratchet is driven to rotate by the bead chain; and the second angle detector is used to measure the rotation angle of the ratchet.

In an embodiment of the present inventive concept, the first angle detector is further used to transmit the rotation angle of the roller to an outer computing device which converts the rotation angle of the roller to the length of the limb; and the second angle detector is further used to transmit the rotation angle of the ratchet to an outer computing device which converts the rotation angle of the ratchet to the circumference of the limb.

In an embodiment of the present inventive concept, the computing device is a mobile device or a computer.

In an embodiment of the present inventive concept, the apparatus for measurement of a limb circumference further comprises a first connecting rod module. In the embodiment, the roller is disposed at the first connecting rod module, so as the roller is alongside the surface of the limb.

In an embodiment of the present inventive concept, the apparatus for measurement of a limb circumference further comprises a double pull string module. In the embodiment, the roller is disposed at the double pull string module, so as the roller is alongside the surface of the limb.

In an embodiment of the present inventive concept, the pull string module further comprises a constant-force spring set; and a connecting wire having two ends. One end of the connecting wire is connected to the constant-force spring set; and wherein the surrounding component is a measurement wire, and the measurement wire is connected to the other end of the connecting wire.

In an embodiment of the present inventive concept, the measurement wire is a long, thin material which is made of at least one selected from the group consisted of plastic, metal and cotton thread, and the measurement wire is flexible and unstretchable.

In an embodiment of the present inventive concept, the first measurement module comprises a first optical motion sensor which is used to measure the length of the limb.

In an embodiment of the present inventive concept, the second measurement module comprises a second optical motion sensor which is used to measure the circumference of the limb.

In an embodiment of the present inventive concept, the first optical motion sensor is further used to transmit the length of the limb to an outer computing device; and the second optical motion sensor is further used to transmit the length of the encircling part to an outer computing device. In an embodiment of the present inventive concept, the computing device is a mobile device or a computer.

In an embodiment of the present inventive concept, the apparatus for measurement of a limb circumference further comprises at least one guide block which is disposed on the measurement wire.

In an embodiment of the present inventive concept, the apparatus for measurement of a limb circumference further comprises a second connecting rod module. In the embodiment, the at least one guide block is disposed at the second connecting rod module, so as the at least one guide block is alongside the surface of the limb.

In an embodiment of the present inventive concept, the apparatus for measurement of a limb circumference comprises a plurality of guide blocks, and the second connecting rod module comprises a frame, a parallel connecting rod, a first connecting rod and a second connecting rod. The frame substantially surrounds the limb, and a slot is disposed on the frame. The parallel connecting rod has two ends, and one end of the parallel connecting rod is engaged in the slot. The first connecting rod may be located above the parallel connecting rod, and the first connecting rod has two ends one of which is engaged in the slot. The second connecting rod may be located above the parallel connecting rod, and the second connecting rod has two ends one of which is connected to the first connecting rod. Wherein the frame, the parallel connecting rod, the first connecting rod and the second connecting rod are connected to the corresponding guide blocks respectively.

In an embodiment of the present inventive concept, the apparatus for measurement of a limb circumference further comprises a third connecting rod module. The third connecting rod module comprises a handle used to be held by a user, and wherein the constant-force spring set is disposed on the handle; a third connecting rod, having a first end and a second end, wherein the first end of the third connecting rod is connected to the handle; and a fourth connecting rod, having a first end and a second end, wherein the first end of the fourth connecting rod is connected to the second end of the third connecting rod, and the second end of the fourth connecting rod is connected to the at least one guide block; and wherein the third connecting rod and the fourth connecting rod are substantially set around the limb and fasten the at least one guide block.

The present invention further provides a device for measurement of a limb compliance, comprising two pull string modules, at least one first measurement module, and two second measurement modules. Each of the pull string module comprises a surrounding component, wherein the surrounding component comprises an encircling part disposed around a limb of an individual, the two pull string modules are next to each other, and wherein the two pull string modules are pulled by different tensions; the at least one first measurement module is disposed at one of the two pull string modules, and wherein the first measurement module is used to move alone the longitudinal axis of the limb and measure the length of the limb meanwhile; and the two second measurement modules are disposed at the two pull string modules, respectively, and each of the second measurement module is used to measure the length of the corresponding encircling part simultaneously when the corresponding first measurement module move alone the limb, so as to determine the limb circumference.

The present invention provides a device used in the treatment of lymphedema, comprising a plurality of pull string modules. Each of the pull string module comprises a surrounding component, wherein the surrounding component comprises an encircling part disposed around a limb of an individual, and the plurality of pull string modules are next to each other, and wherein each of the pull string modules is pulled by default tensions.

In an embodiment of the present inventive concept, the device used in the treatment of lymphedema further comprises at least one first measurement module and at least one second measurement modules. The at least one first measurement module is disposed at one of the plurality of pull string modules, and wherein the first measurement module is used to move alone the longitudinal axis of the limb and measure the length of the limb simultaneously; and the at least one second measurement modules is disposed at the pull string module where the at least one first measurement module disposed, and the second measurement module is used to measure the length of the corresponding encircling part simultaneously when the corresponding first measurement module move alone the limb, so as to determine the limb circumference.

Compared to the prior art, the apparatus for measurement of a limb circumference of the present invention is able to measure the limb circumference simultaneously and continuously. The present invention further provides a device including two apparatuses of the present invention to measure the limb compliance while measuring the limb circumference and a device including a plurality of the apparatuses of the present invention to be used for treatment of lymphedema. The apparatus for measurement of a limb circumference of the present invention is capable of building a whole data collection of the appearance of a limb during one-time measurement and being used in the treatment of lymphedema, which is practical assistive device in medication and rehabilitation.

DETAILED DESCRIPTION

The present invention is described by the following specific embodiments. Those with ordinary skills in the arts can readily understand other advantages and functions of the present invention after reading the disclosure of this specification. Any changes or adjustments made to their relative relationships, without modifying the substantial technical contents, are also to be construed as within the range implementable by the present invention.

Figure 1:
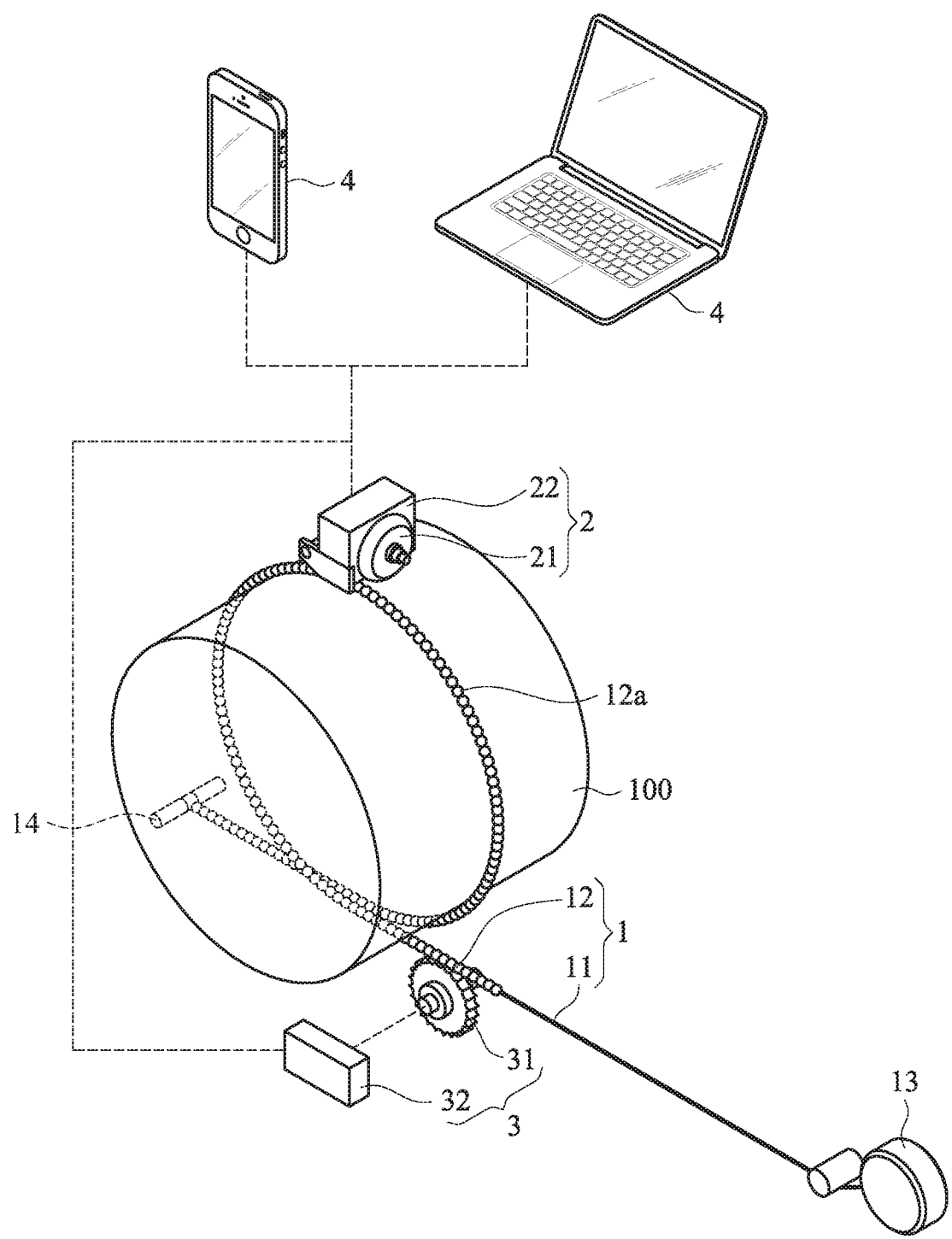
FIG. 1 illustrates a schematic view of one exemplary embodiment of the apparatus for measurement of a limb circumference according to the present inventive concept.

Please refer to FIG. 1 which illustrates a schematic view of one exemplary embodiment of the apparatus for measurement of a limb circumference according to the present inventive concept. The present invention provides an apparatus for measurement of a limb circumference, comprising a pull string module 1, a first measurement module 2, and a second measurement module 3. The pull string module 1 may comprise a surrounding component, wherein the surrounding component may comprise an encircling part disposed around a limb 100 of an individual. The first measurement module 2 and the second measurement module 3 may be disposed at the pull string module. The first measurement module 2 may move alone the longitudinal axis of the limb 100 and meanwhile measure the length of the limb; and the second measurement module 3 may measure the length of the encircling part 12a simultaneously when the first measurement module 2 move alone the limb 100 to determine the limb circumference. In the present invention, the limb 100 may be upper limbs and/or lower limbs. The present invention is demonstrated by upper limbs in the following exemplary embodiments. However, a person having ordinary skills in the art realize the present invention can be used in lower limbs as well.

In the exemplary embodiment in FIG. 1, the pull string module 1 may further comprise a connecting wire 11 having two ends, the surrounding component may be a bead chain 12 which is disposed to one end of the connecting wire 11. The bead chain 12 may be flexible and unstretchable. The first measurement module 2 may comprise a roller 21 and a first angle detector 22 connected to the roller. The first angle detector 22 is used to measure the rotation angle of the roller 21. The second measurement module may comprise a ratchet 31 and a second angle detector 32. The ratchet 31 may be disposed on the bead chain 12. The second angle detector 32 may be connected to the ratchet 31. The second angle detector 32 is used to measure the rotation angle of the ratchet 31.

In the exemplary embodiment of the present inventive concept, the surrounding component may be a bead chain 12, and the bead chain 12 may comprise an encircling part 12a which may be a part of the bead chain 12 which is disposed around a limb 100 of an individual (e.g. arms). The bead chain 12 may be flexible and unstretchable. The roller 21 may be placed on the arm and may roll from the desired starting point. More specifically, the roller 21 may roll and move alone the longitudinal axis of the arm, meanwhile the first angle detector 22 would measure the rotation angle of the roller 21. The first angle detector 22 may further transmit the rotation angle of the roller to an outer computing device 4, such as a mobile device or a computer. The outer computing device 4 may convert the rotation angle of the roller to the distance which the first measurement module 2 moves. For example, if the roller 21 rolls from the starting point of the arm to the end of the arm, the distance which the first measurement module 2 moves would be the length of the arm.

In the exemplary embodiment of the present inventive concept, when the apparatus of the present invention move alone the longitudinal axis of the arm, the circumference of the arm may be varied because of the variation of the thickness through the whole arm. The encircling part 12a would be elongated or shortened by the tension from the connecting wire 11. In one exemplary embodiment of the present inventive concept, the pull string module may further comprise a constant-force spring set 13 and a fixed axis 14. In this embodiment, the constant-force spring set 13 may be a spring with a default elastic constant. One end of the bead chain 12 may be connected to the fixed axis 14 and the other end of the bead chain 12 may be connected to one end of the connecting wire 11, and the other end of the connecting wire 11 may be connected to the constant-force spring set 13. The constant-force spring set 13 may comprise spiral spring coil. In another embodiment of the present inventive concept, the apparatus of the present invention may further comprise a bead chain pulley (not shown in the figures) located on the fixed axis 14. In this embodiment, one end of the bead chain 12 may be connected to one end of the connecting wire 11. The bead chain 12 may wrap the bead chain pulley, and the other end of the bead chain 12 may be connected back to the connecting wire 11. By doing so, the move distance of the bead chain 12 and that of the connecting wire 11 may be reduced. The length of the encircling part 12a may vary with the circumference of the arm; spiral spring coil inside the constant-force spring set 13 may stretch and pull the connecting wire 11 and the bead chain 12 to maintain the fix tension on the connecting wire and the bead chain. The ratchet 31 may be engaged with the bead chain 12, so the ratchet 31 is driven to rotate by the bead chain 12. The second angle detector 32 may measure the rotation angle of the ratchet 31 at every position of the arm. The second angle detector 32 may further transmit the rotation angle of the ratchet 31 to an outer computing device 4, such as a mobile device or a computer. The outer computing device 4 may convert the rotation angle of the ratchet to the length of the encircling part 12a of the bead chain 12 which is the circumference of the limb 100.

Figure 2:
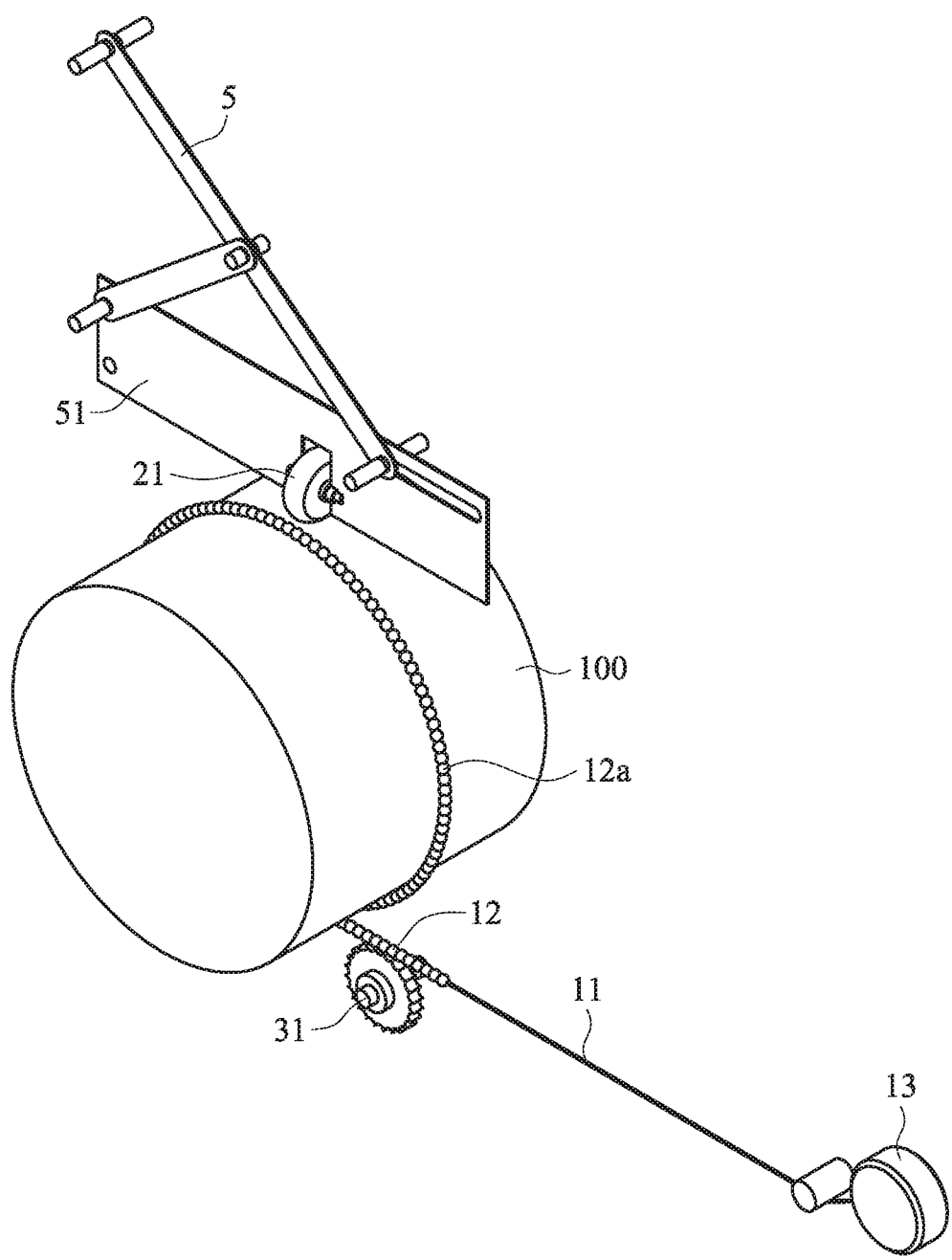
FIG. 2 illustrates a schematic view of the first connecting rod module in one exemplary embodiment according to the present inventive concept.

Please refer to FIG. 2 which illustrates a schematic view of the first connecting rod module in one exemplary embodiment according to the present inventive concept. The apparatus for measurement of a limb circumference according to the present inventive concept may further comprise a first connecting rod module 5. The first connecting rod module 5 is design by the geometry of midpoint of hypotenuse of right triangle being circumcenter. Roller 21 may be disposed at a parallel panel 51 under the first connecting rod module 5. The parallel panel 51 may make the roller 21 vertical to the surface of the limb 100 needed to be measured. The first connecting rod module 5 may further be configured a tension spring (not illustrated). The parallel panel 51 may go down by the tension spring to press the roller 21 to roll alongside the surface of the limb 100. The first connecting rod module 5 may further comprise a trench (not illustrated) disposed below the parallel panel 51. The first connecting rod module 5 may pull the bead chain 12 through the trench, so as the bead chain 12 may move alone the longitudinal axis of the limb 100 with the roller 21.

Figure 3:
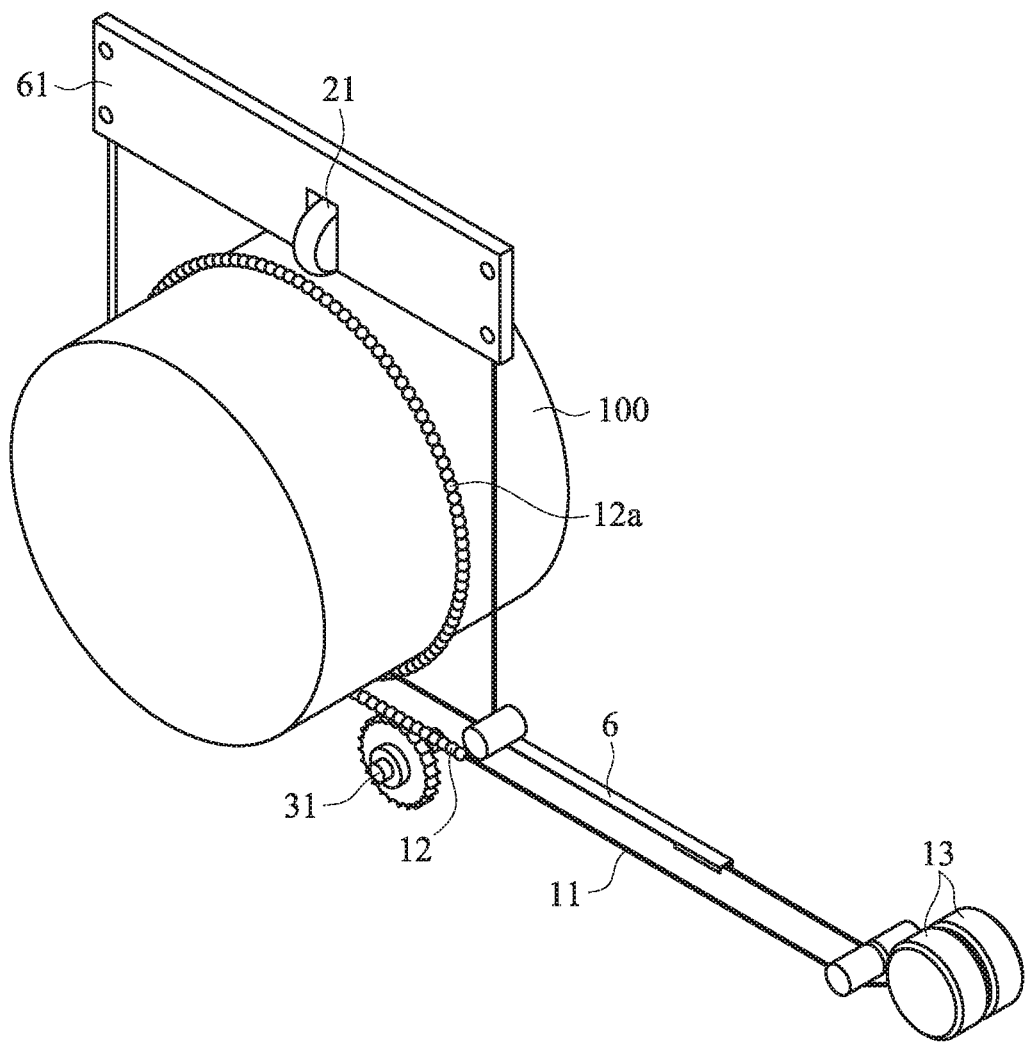
FIG. 3 illustrates a schematic view of the double pull string module in another exemplary embodiment according to the present inventive concept.

Please refer to FIG. 3 which illustrates a schematic view of the double pull string module in another exemplary embodiment according to the present inventive concept. The apparatus for measurement of a limb circumference of the present inventive concept may further comprise a double pull string module 6 whose function is similar with that of the first connecting rod module 5 in FIG. 2. In one exemplary of the present inventive concept, the roller 21 may be disposed on the parallel panel 61 of the double pull string module 6. The parallel panel 61 may be pulled down by the double pull string module 6. The parallel panel 61 may make the roller 21 vertical to the surface of the limb needed to be measured and press the roller 21 to roll alongside the surface of the limb 100. The double pull string module 6 may further comprise a trench (not illustrated) disposed below the parallel panel 61. The double pull string module 6 may pull the bead chain 12 through the trench, so as the bead chain 12 may move alone the longitudinal axis of the limb 100 with the roller 21.

A person having ordinary skills in the art understand that the first connecting rod module 5 in FIG. 2 and the double pull string module 6 in FIG. 3 have similar function. Therefore, the apparatus for measurement of a limb circumference of the present inventive concept may comprise either of them, or both of them.

Figure 4:
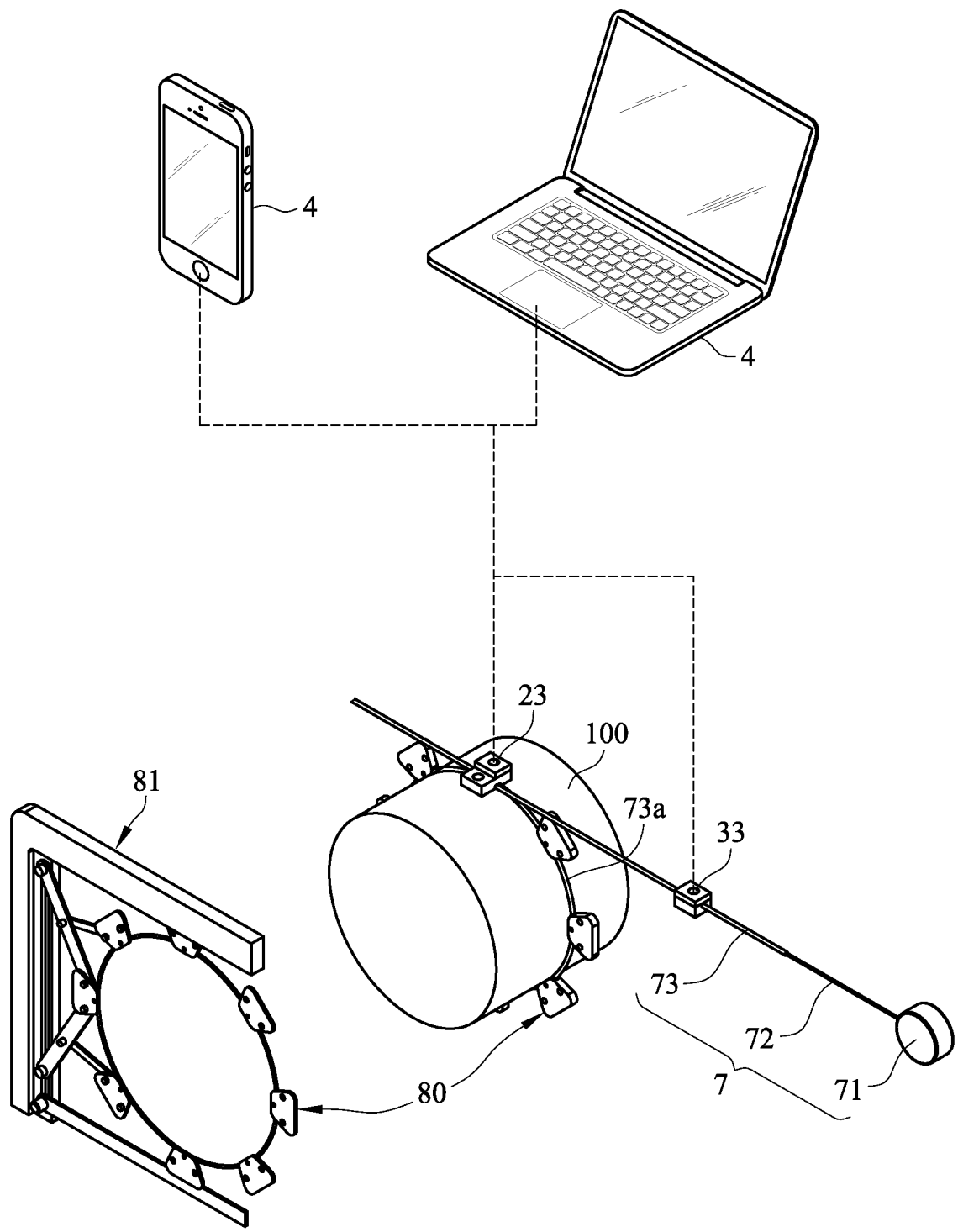
FIG. 4 illustrates a schematic view of another exemplary embodiment according to the present inventive concept.

Please refer to FIG. 4 which illustrates a schematic view of another exemplary embodiment according to the present inventive concept. In the exemplary embodiment according to the present inventive concept, the pull string module 7 may further comprise a surrounding component, a constant-force spring set 71 and a connecting wire 72 having two ends. One end of the connecting wire 72 is connected to the constant-force spring set 71. The surrounding component is a measurement wire 73. The measurement wire 73 may be connected to the other end of the connecting wire 72. In the exemplary embodiment of the present inventive concept, the measurement wire 73 may comprise an encircling part 73a which may be a part of the measurement wire 73 which is disposed around a limb 100 of an individual (e.g. arms). The measurement wire 73 may be made of at least one selected from the group consisted of plastic, metal and cotton thread, and the measurement wire 73 may be flexible and unstretchable.

In the present inventive concept, the rotation angle detector may be replaced by the optical motion sensor. In this exemplary embodiment, The first measurement module 2 and the second measurement module 3 may comprise a first optical motion sensor 23 and a second optical motion sensor 33, respectively. The first optical motion sensor 23 may be disposed at the position of the upper the apparatus for measurement of a limb circumference where contacting the skin. When the apparatus for measurement of a limb circumference of the present inventive concept move alone the longitudinal axis of the limb 100, the first measurement module 2 and the measurement wire 73 may move simultaneously. The first optical motion sensor 23 may sense the distance which the apparatus moves alone the longitudinal axis of the limb 100 to measure the length of the limb 100.

The second optical motion sensor 33 may be disposed closely on the measurement wire 73 to measure the circumference of the limb 100. The second optical motion sensor 33 may measure the circumference of the limb 100 by sensing the distance which the measurement wire 73 moves. Alternatively, the second optical motion sensor 33 may be disposed beside the sidewall of the pulley (not illustrated) which change the direction of the measurement wire 73 to sense the rotation angle of the pulley to measure the circumference of the limb 100. In this embodiment, the movement of the connecting wire 72 and that of the measurement wire 73 are the same, so the second optical motion sensor 33 may be disposed closely on the connecting wire 72 to measure the circumference of the limb 100 by sensing the distance which the connecting wire 72 moves. Alternatively, the second optical motion sensor 33 may be disposed beside the sidewall of the pulley (not illustrated) which change the direction of the connecting wire 72 to sense the rotation angle of the pulley to convert to the distance which the connecting wire 72 moves.

The length of the limb 100 measured by the first optical motion sensor 23 from sensing the distance which the apparatus moves alone the longitudinal axis of the limb 100 and the circumference of the limb 100 measured by the second optical motion sensor 33 from sensing the distance which the measurement wire 73 (or the connecting wire 72) moves may be transmitted to an outer computing device 4, such as a mobile device or a computer. Alternatively, the rotation angle sensed by the second optical motion sensor 33 may be transmitted to an outer computing device 4 to convert to the distance which the measurement wire 73 (or the connecting wire 72) moves, which represents the circumference of the limb 100.

Figure 5:
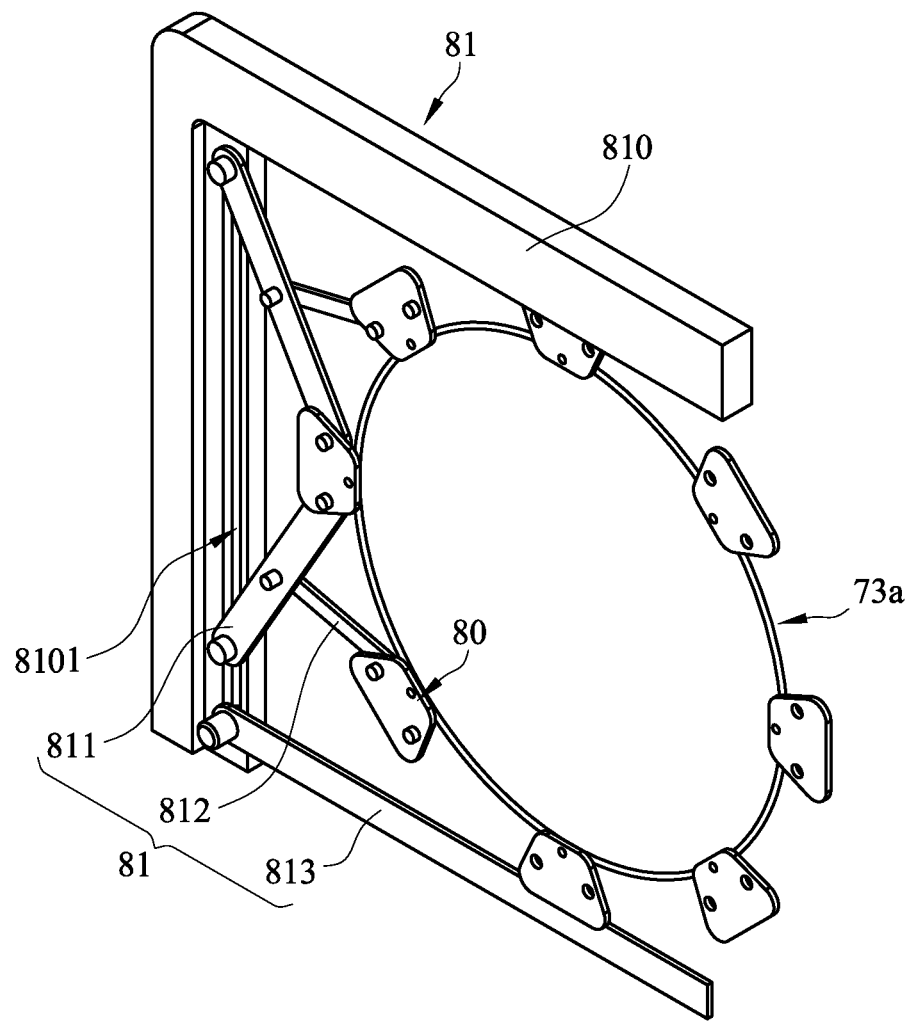
FIG. 5 illustrates a schematic view of the second connecting rod module in another exemplary embodiment according to the present inventive concept.

Please refer to FIGS. 4 and 5. FIG. 5 illustrates a schematic view of the second connecting rod module in another exemplary embodiment according to the present inventive concept. The apparatus for measurement of a limb circumference of the present inventive concept may further comprise at least one guide block 80 and a second connecting rod module 81. In this embodiment, the apparatus for measurement of a limb circumference of the present inventive concept comprises a plurality of guide blocks 80. The plurality of guide blocks 80 may be disposed on the encircling part 73a of the measurement wire 73 evenly or unevenly and surround the limb 100. The second connecting rod module 81 may be disposed at both side and bottom of the apparatus or measurement of a limb circumference. Each of the plurality of guide blocks 80 may be further disposed at the second connecting rod module 81 to make the plurality of guide blocks alongside the surface of the limb 100. By doing so, the measurement wire 73 may be alongside the surface of the limb 100 when the apparatus for measurement of a limb circumference of the present inventive concept moves.

More specifically, the second connecting rod module 81 may comprise a frame 810, a first connecting rod 811, a second connecting rod 812 and a parallel connecting rod 813. The frame 810 may substantially surround the limb, and a slot 8101 may be disposed on the frame, wherein the slot 8101 may be substantially perpendicular to the longitudinal axis of the limb. The parallel connecting rod 813 has two ends, and one end of the parallel connecting rod 813 may be slidably engaged in the slot 8101 and substantially perpendicular to the slot 8101. The first connecting rod 811 has two ends and one end of the first connecting rod 811 may be slidably engaged in the slot 8101. The second connecting rod 812 has two ends and one end of the second connecting rod 812 may be pivotably connected to the first connecting rod 811. The frame 810, the parallel connecting rod 813, the first connecting rod 811 and the second connecting rod 812 may be connected to the corresponding guide blocks 80 respectively. The parallel connecting rod 813 may be disposed near the bottom of the apparatus or measurement of a limb circumference and under the limb and the first connecting rod 811 and the second connecting rod 812 may be located above the parallel rod 813 to guide the measurement wire 73 alongside the surface of the limb 100. The parallel connecting rod 813 may be designed as the first connecting rod module 5 shown in FIG. 5 or the double pull string module 6 in FIG. 3.

Figure 6:
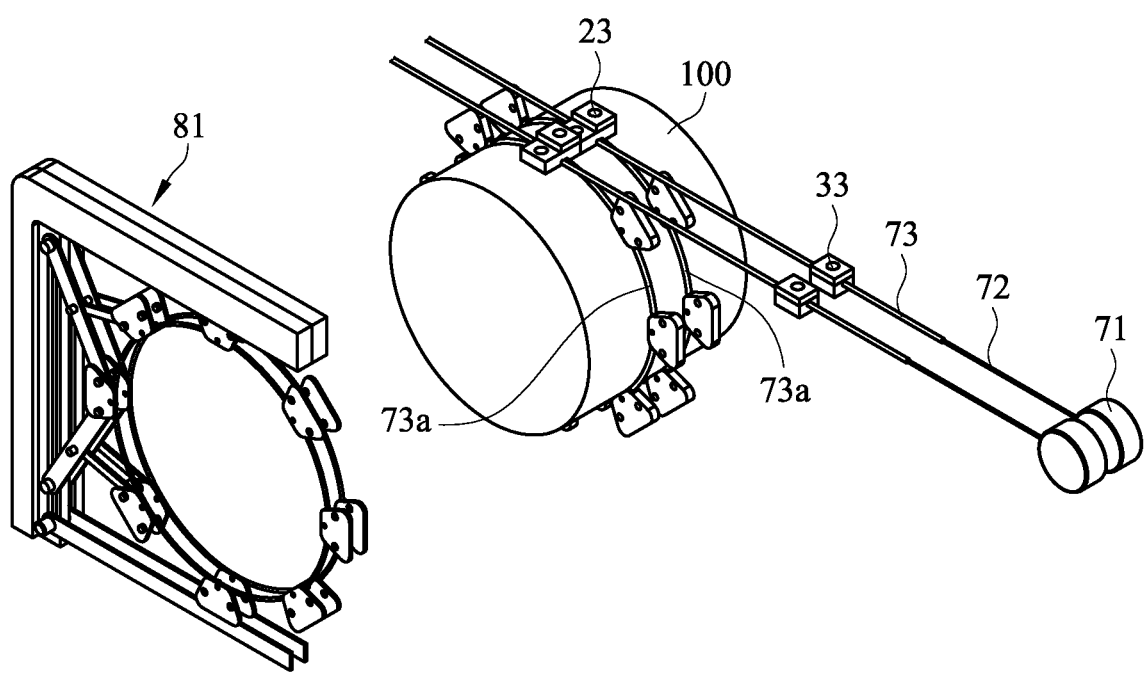
FIG. 6 illustrates a schematic view of one exemplary embodiment of the a device for measurement of a limb compliance according to the present inventive concept.

Please refer to FIG. 6 which illustrates a schematic view of one exemplary embodiment of the a device for measurement of a limb compliance according to the present inventive concept. The device for measurement of a limb compliance according to the present inventive concept may comprise two pull string modules 7, each of which includes a constant-force spring set 71, a connecting wire 72 and a measurement wire 73; at least one first measurement module 2 including a first optical motion sensor 23; and two second measurement modules 3, each of which includes a second optical motion sensor 33. The two pull string modules 7 may comprise a surrounding component, wherein the surrounding component may comprise an encircling part disposed around a limb 100 of an individual; the two pull string modules 7 may be next to each other, and wherein the two pull string modules 7 may be pulled by different tensions to determine the variation of the compliance (limb stiffness). The first optical motion sensor 23 may be disposed at one or both of the pull string modules 7 to move alone the longitudinal axis of the limb 100 and sense the length of the limb meanwhile. Each of the two second optical motion sensor 33 may be disposed at the corresponding pull string modules 7 to sense the length of the corresponding encircle part 73a of each of the pull string module to determine the limb circumference simultaneously when the first optical motion sensor 23 moves alone the longitudinal axis of the limb 100.

The device for measurement of a limb compliance according to the present inventive concept may comprise one apparatus for measurement of a limb circumference of the present inventive concept combined with at least one pull string module 7. Preferably, the pull string modules may be aligned. More preferably, each of the pull string modules may be optionally conducted by same or different tensions and yet move simultaneously alone the longitudinal axis of the limb 100, which means, the device for measurement of a limb compliance is able to collect the data of the limb circumferences measured by different tensions (i.e. tightness of the measurement wire) at the same position, wherein the difference between the values of the two limb circumferences may be converted to the stiffness of the limb. In other words, the tightness of the measurement wires caused by the different tension results in different measured values of the limb circumference. The difference between the two measured values of the limb circumference reflects the limb compliance, so the change of the limb compliance may be monitored.

Figure 7:
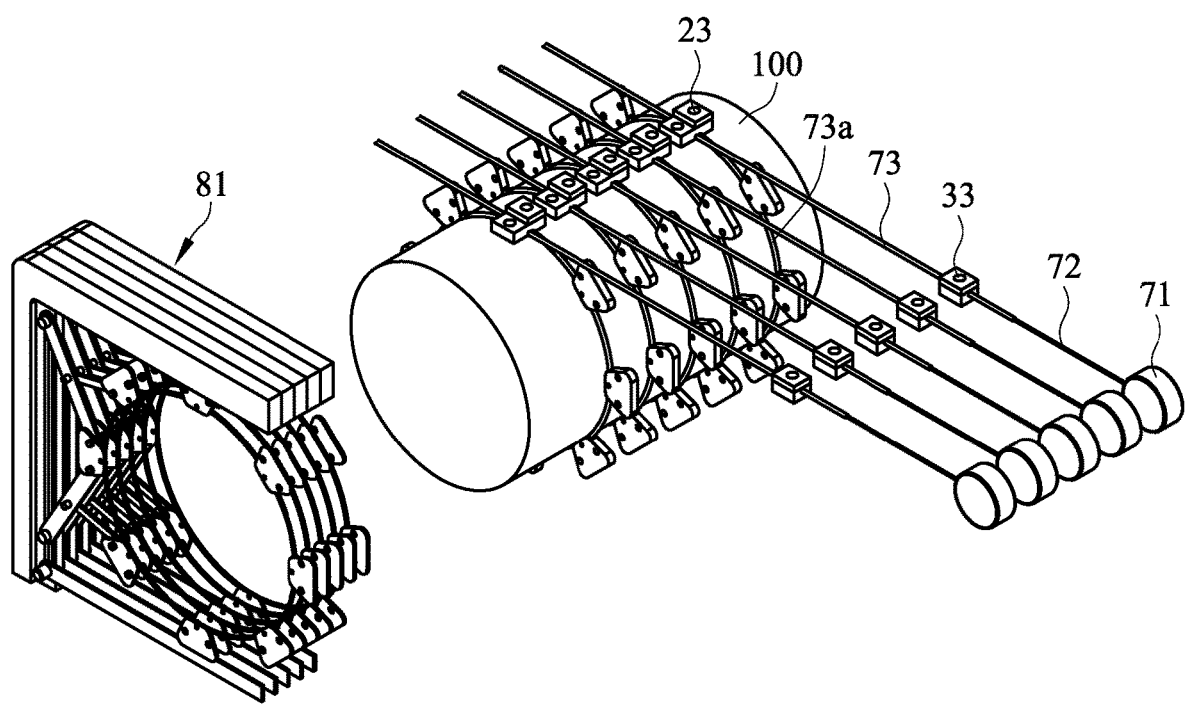
FIG. 7 illustrates a schematic view of one exemplary embodiment of the a device used in the treatment of lymphedema according to the present inventive concept.

Please refer to FIG. 7 which illustrates a schematic view of one exemplary embodiment of the a device used in the treatment of lymphedema according to the present inventive concept. The device used in the treatment of lymphedema according to the present inventive concept may comprise one apparatus for measurement of a limb circumference of the present inventive concept combined with a plurality of pull string modules 7, each of which includes a constant-force spring set 71, a connecting wire 72 and a measurement wire 73. Each of the pull string module 7 may comprise a surrounding component, wherein the surrounding component may comprise an encircling part 73a disposed around a limb 100 of an individual, and the plurality of pull string modules 7 may be next to each other, and wherein each of the pull string modules 7 is pulled by default tensions. More specifically, each of the tensions on the constant-force spring set 71 of the pull string modules may be differed due to the treatments. In one exemplary embodiment of the present inventive concept, the device used in the treatment of lymphedema may comprise at least one first measurement module 2 including a first optical motion sensor 23; and at least one second measurement modules 3, each of which includes a second optical motion sensor 33. The at least one first measurement module 23 may be disposed at one of the plurality of pull string modules 7, and the first measurement module moves alone the longitudinal axis of the limb 100 and meanwhile measure the length of the limb 100. The at least one second measurement modules 33 may be disposed at the same pull string module 7 where the at least one first measurement module 23 disposed. The second measurement module 33 is used to measure the length of the corresponding encircling part 73a simultaneously when the corresponding first measurement module 23 moves alone the limb 100, so as to determine the limb circumference.

In some embodiments, the spacing between every pull string modules 7 may be adjusted by the condition of the patients or by the design of the device. Preferably, the spacing may be 10~100 mm, but not limited.

As shown in FIG. 7, the device used in the treatment of lymphedema according to the present inventive concept may comprise one apparatus for measurement of a limb circumference of the present inventive concept combined with a plurality of pull string module. Each of the constant-force spring set of the plurality of pull string modules is pulled by different tensions. Preferably, the device used in the treatment of lymphedema according to the present inventive concept may comprise one apparatus for measurement of a limb circumference of the present inventive concept and 2 to 9 pull string modules, but not limited. According to this exemplary embodiment, the elastic constants of each of the constant-force spring set 71 are different. When the device used in the treatment of lymphedema is pulled alone the limb 100, forces would be applied on the surface of the limb 100 by each of the measurement wires 73 at the same time to relieve lymphedema. The therapeutic effect is caused by appropriate pressure being applied on the lesion which would excite the contraction of the smooth muscle around the lymphatic vessels. The lymph fluid in the tissues may be further guided to the superficial circulation by drainage and through any anastomoses in the superficial circulation to a normal lymph node and back the vascular system.

Figure 8:
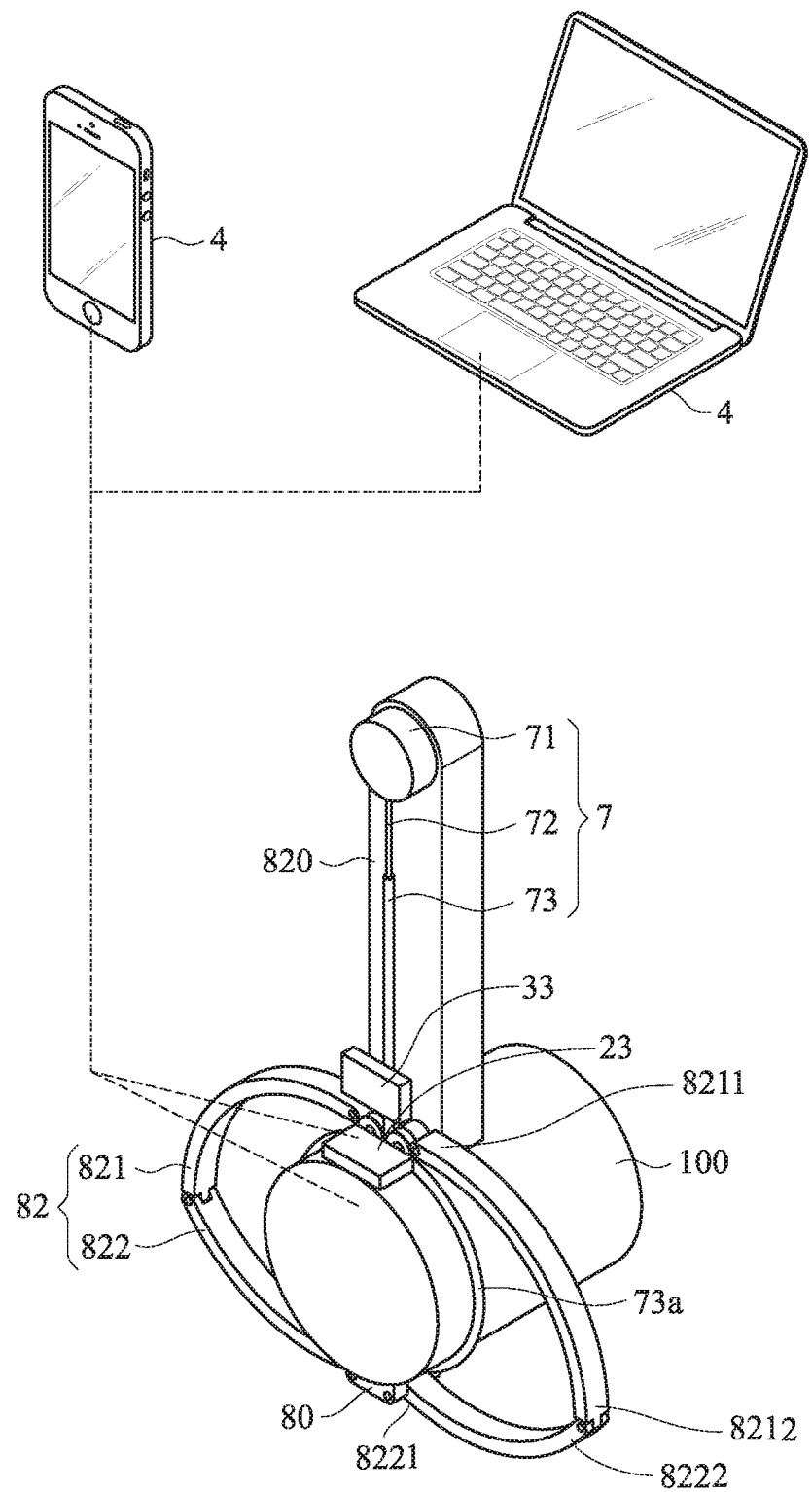
FIG. 8 illustrates a schematic view of another exemplary embodiment according to the present inventive concept.

FIG. 8 illustrates a schematic view of another exemplary embodiment according to the present inventive concept. As shown in FIG. 8, the apparatus for measurement of a limb circumference of the present inventive concept may further comprise a third connecting rod module 82 and at least one guide block 80. The third connecting rod module 82 may comprise a handle 820; two third connecting rods 821, each of which has a first end 8211 and a second end 8212, and two fourth connecting rods 822, each of which has a first end 8221 and a second end 8222. The handle 820 may be used to be held by a user, and wherein the constant-force spring set 71 may be disposed on the handle 820. The first end 8211 of the third connecting rod 821 may be connected to the handle 820. The second end 8212 of the third connecting rod 821 may be connected to the first end 8221 of the fourth connecting rod 822. The second end 8222 of the fourth connecting rod 822 may be connected to the guide block 80. The two third connecting rod 821 and the two fourth connecting rod 822 may be substantially set around the limb 100 and fasten the guide block 80. The guide block 80 may make the encircling part 73a of the measurement wire 73 alongside the surface of the limb 100 and guide the measurement wire 73 to slide alone the longitudinal axis of the limb 100. The third connecting rod module 82 and the guide block 80 may be driven by the constant-force spring set 71 connected to the other end of the measurement wire 73.

Figure 9:
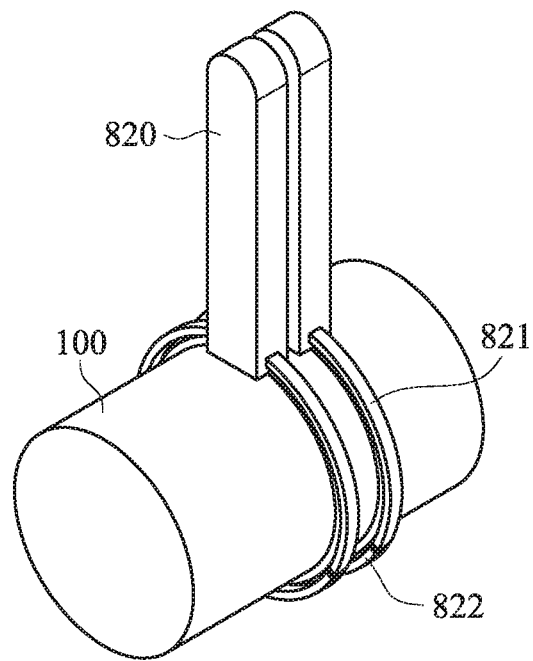
FIG. 9 illustrates a schematic view of another exemplary embodiment of the a device for measurement of a limb compliance according to the present inventive concept.
Figure 10:
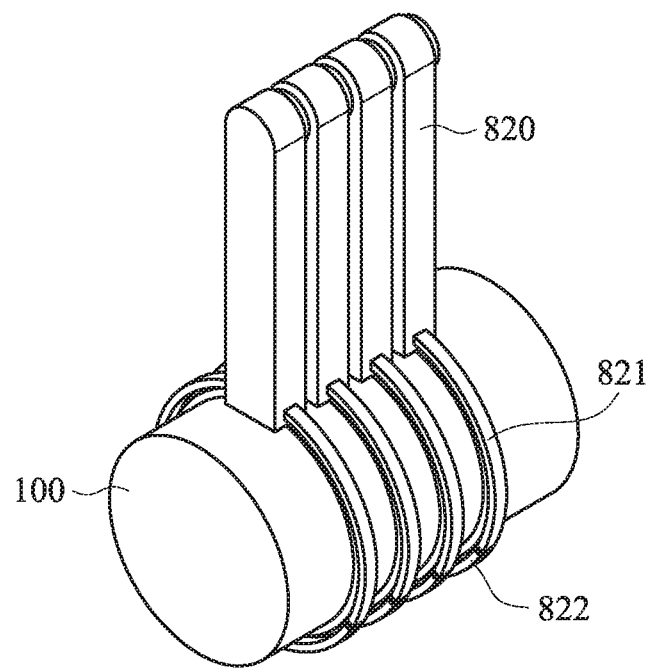
FIG. 10 illustrates a schematic view of another exemplary embodiment of the a device used in the treatment of lymphedema according to the present inventive concept.

As shown in FIG. 9, the device for measurement of a limb compliance according to the present inventive concept may comprise two apparatuses for measurement of a limb circumference comprising the third connecting rod 82. Likewise, the device used in the treatment of lymphedema according to the present inventive concept may comprise a plurality of apparatuses for measurement of a limb circumference comprising the third connecting rod 82, as shown in FIG. 10. The device used in the treatment of lymphedema according to the present inventive concept may comprise 3 to 10 apparatuses for measurement of a limb circumference of the present inventive concept, but not limited.

In summary, the present invention provides an apparatus for measurement of a limb circumference move alone the longitudinal axis of the limb and meanwhile continuously measure the limb circumference in situ and transmit the value to a mobile device or a computer via Bluetooth or any other connection way for recordation and further analysis used for the evaluation of the circumference and volume of a limb. Besides, the present invention further provides a device including one apparatus for measurement of a limb circumference of the present invention combined with at least one pull string module to measure the limb compliance and to be used in the treatment of lymphedema.

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:

1. An apparatus for measurement of a limb circumference, comprising:
   a pull string module, comprising a surrounding component, wherein the surrounding component comprises an encircling part disposed around a limb of an individual, wherein the surrounding component is a bead chain;
   a first measurement module disposed at the pull string module, and wherein the first measurement module is used to move along the longitudinal axis of the limb and meanwhile measure the length of the limb and wherein the first measurement module comprises a roller connected to the bead chain, and the roller is used to roll along the longitudinal axis of the limb;
   a second measurement module disposed at the pull string module, and the second measurement module is used to measure the length of the encircling part simultaneously when the first measurement module move along the limb, so as to determine the limb circumference; and
   a first connecting rod module or a double pull string module, wherein the roller is disposed at the first connecting rod module or the double pull string module, so as the roller is alongside the surface of the limb.

2. The apparatus for measurement of a limb circumference of claim 1, wherein the pull string module comprises:
   a constant-force spring set;
   a connecting wire having two ends, and one end of the connecting wire is connected to the constant-force spring set; and wherein
   the bead chain is connected to the other end of the connecting wire.

3. The apparatus for measurement of a limb circumference of claim 2, wherein the first measurement module comprises:
   a first angle detector connected to the roller, and the first angle detector is used to measure the rotation angle of the roller.

4. The apparatus for measurement of a limb circumference of claim 3, wherein the second measurement module comprises:
   a ratchet disposed on the bead chain, and wherein the ratchet is driven to rotate by the bead chain; and
   a second angle detector connected to the ratchet, and the second angle detector is used to measure the rotation angle of the ratchet.

5. The apparatus for measurement of a limb circumference of claim 4, wherein the first angle detector is further used to transmit the rotation angle of the roller to an outer computing device which converts the rotation angle of the roller to the length of the limb; and the second angle detector is further used to transmit the rotation angle of the ratchet to an outer computing device which converts the rotation angle of the ratchet to the circumference of the limb.

6. The apparatus for measurement of a limb circumference of claim 5, wherein the computing device is a mobile device or a computer.

* * * * *